(12) United States Patent
Certa et al.

(10) Patent No.: US 6,422,249 B1
(45) Date of Patent: Jul. 23, 2002

(54) CARTRIDGE WASHING SYSTEM AND METHODS

(75) Inventors: Ulrich Certa, Allschwil; Hansjörg Tschirky, Ettingen, both of (CH)

(73) Assignee: Affymetrix Inc., Santa Clara, CA (US)

(*) Notice: Subject to any disclaimer, the term of this patent is extended or adjusted under 35 U.S.C. 154(b) by 175 days.

(21) Appl. No.: 09/636,517

(22) Filed: Aug. 10, 2000

(51) Int. Cl.$^7$ .................................................. B08B 9/20

(52) U.S. Cl. ............................... 134/168 R; 134/169 R

(58) Field of Search ........................ 134/166 R, 167 R, 134/168 R, 169 R, 62

(56) References Cited

U.S. PATENT DOCUMENTS

| | | | |
|---|---|---|---|
| 4,665,034 A | 5/1987 | Chandler | 435/287 |
| 4,764,671 A | 8/1988 | Park | 250/227 |
| 4,829,010 A | 5/1989 | Chang | 422/58 |
| 4,859,419 A | 8/1989 | Marks et al. | 422/56 |
| 4,889,611 A | 12/1989 | Blough | 204/409 |
| 5,104,808 A | 4/1992 | Laska et al. | 436/48 |
| 5,133,374 A | * 7/1992 | Druding et al. | 134/169 R |
| 5,143,854 A | 9/1992 | Pirrung et al. | 436/518 |
| 5,154,888 A | 10/1992 | Zander et al. | 422/58 |
| 5,170,659 A | 12/1992 | Kemp | 73/46 |
| 5,184,634 A | * 2/1993 | Kitajima | 134/166 R X |
| 5,229,297 A | 7/1993 | Schniplesky et al. | 436/94 |
| 5,230,866 A | 7/1993 | Shartle et al. | 422/103 |
| 5,258,781 A | 11/1993 | John | 346/140 |
| 5,279,721 A | 1/1994 | Schmid | 204/182.8 |
| 5,288,463 A | 2/1994 | Chemelli | 422/58 |
| 5,296,195 A | 3/1994 | Pang et al. | 422/82.05 |
| 5,352,609 A | 10/1994 | Bouqet et al. | 435/270 |
| 5,384,261 A | 1/1995 | Winkler et al. | 436/518 |
| 5,395,587 A | 3/1995 | Brigham-Burke et al. | 422/68.1 |
| 5,422,271 A | 6/1995 | Chen et al. | 435/287 |
| 5,424,186 A | 6/1995 | Fodor et al. | 536/22.1 |
| 5,486,335 A | 1/1996 | Wilding et al. | 422/55 |
| 5,489,678 A | 2/1996 | Fodor et al. | 536/22.1 |
| 5,500,187 A | 3/1996 | Deoms et al. | 422/58 |
| 5,543,329 A | 8/1996 | Bedell | 435/7.32 |
| 5,578,832 A | 11/1996 | Trulson et al. | 250/458.1 |
| 5,587,128 A | 12/1996 | Wilding et al. | 422/250 |
| 5,593,838 A | 1/1997 | Zanzucchi et al. | 435/6 |
| 5,593,839 A | 1/1997 | Hubbell et al. | 435/6 |
| 5,595,908 A | 1/1997 | Fawcett et al. | 435/287.2 |
| 5,599,504 A | 2/1997 | Hosoi et al. | 422/82.08 |
| 5,627,041 A | 5/1997 | Shartle | 435/7.24 |
| 5,635,358 A | 6/1997 | Wilding et al. | 435/7.2 |
| 5,637,469 A | 6/1997 | Wilding et al. | 435/7.2 |

(List continued on next page.)

FOREIGN PATENT DOCUMENTS

| | | |
|---|---|---|
| WO | WO 89/10977 | 11/1989 |
| WO | WO 89/11548 | 11/1989 |
| WO | WO 90/15070 | 12/1989 |
| WO | WO 93/09668 | 5/1992 |
| WO | WO 92/10092 | 6/1992 |
| WO | WO 95/33846 | 12/1995 |

OTHER PUBLICATIONS

Fodor et al., "Light–Directed, Spatially Addressable Parallel Chemical Synthesis", Science, 251: 767–777 (1991).
*Physical Acoustics, Principles and Methods.* vol. 2, Part B, Mason, ed., Academic Press, (1965).
*Piezoelectric Technology, Data for Engineers*, Clevite Corp.
Sjolander et al. Anal Chem. vol. 63 pp. 2338–2345, 1991.

*Primary Examiner*—Philip Coe
(74) *Attorney, Agent, or Firm*—Townsend and Townsend and Crew LLP

(57) ABSTRACT

A washing system comprises a support for holding several cartridges. Each cartridge has a chamber with an inlet and an outlet. Wash blocks are movably coupled to the support, each having two needles for penetrating the inlet and the outlet of a respective cartridge when the wash blocks are moved towards the support. Tubing is coupled to the needles for flowing liquid through the chamber of the cartridge.

17 Claims, 6 Drawing Sheets

U.S. PATENT DOCUMENTS

| | | | |
|---|---|---|---|
| 5,652,149 A | 7/1997 | Mileaf et al. | 435/518 |
| 5,658,802 A | 8/1997 | Hayes et al. | 436/518 |
| 5,674,743 A | 10/1997 | Ulmer | 435/287.2 |
| 5,675,700 A | 10/1997 | Atwood et al. | 392/382 |
| 5,683,916 A | 11/1997 | Goffe et al. | 436/535 |
| 5,698,450 A | 12/1997 | Ringrose et al. | 436/525 |
| 5,716,825 A | 2/1998 | Hancock et al. | 435/286.5 |
| 5,726,010 A | 3/1998 | Clark | 435/5 |
| 5,726,013 A | 3/1998 | Clark | 435/5 |
| 5,812,511 A | 9/1998 | Kawamura et al. | 369/77.2 |
| 5,834,758 A | 11/1998 | Trulson et al. | |
| 5,869,004 A | 2/1999 | Parce et al. | 422/100 |
| 5,945,334 A | 8/1999 | Besemer et al. | |
| 6,025,601 A | 2/2000 | Trulson et al. | |
| 6,050,278 A * | 4/2000 | Arnal et al. | 134/167 R |
| 6,114,122 A | 9/2000 | Besemer et al. | |
| 6,170,494 B1 * | 1/2001 | Marinaro et al. | 134/166 R X |
| 6,308,721 B1 * | 10/2001 | Bock et al. | 134/166 R |

* cited by examiner

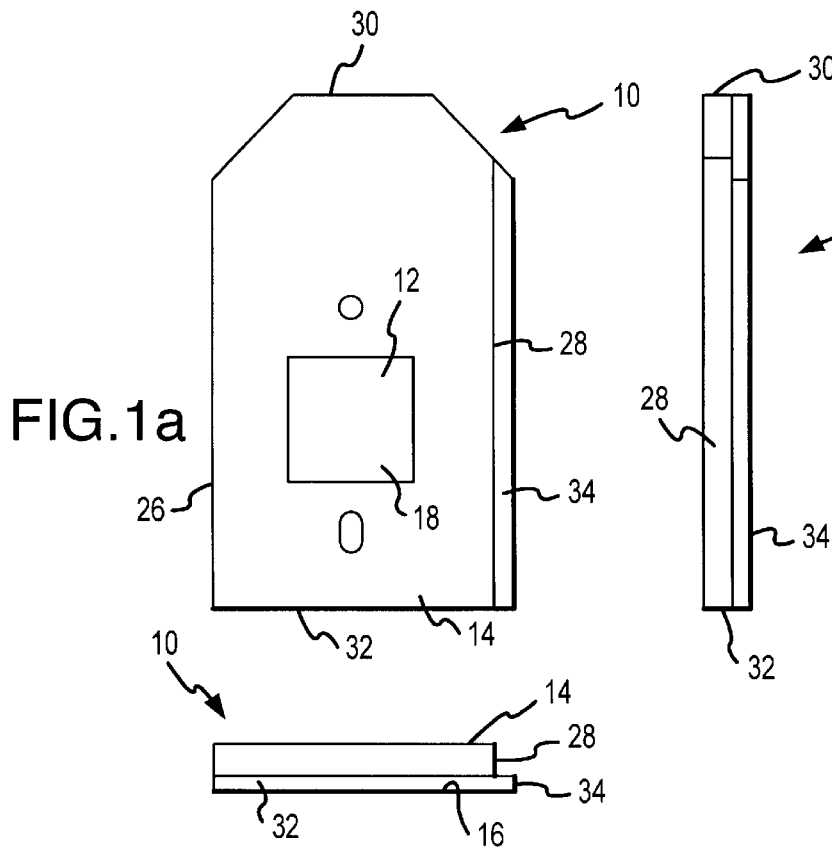
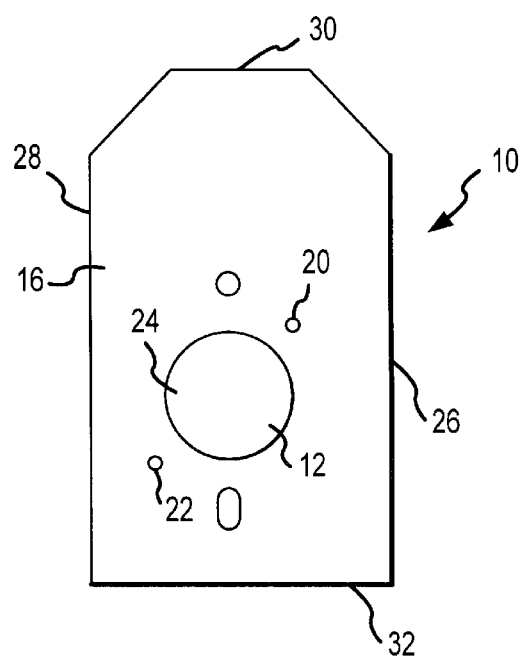

CARTRIDGE WASHING SYSTEM AND METHODS

FIELD OF THE INVENTION

The invention relates to a washing system and method for circulating a liquid through one or more cartridges that each include a chamber having an inlet and an outlet.

BACKGROUND OF THE INVENTION

Fluidics stations have been developed for carrying out repeated hybridizations of a target nucleic acid to a polymeric array of nucleic acid probes. Such stations are described in, for example, copending U.S. patent application Ser. No. 09/510,805, previously incorporated by reference. Such fluidics stations typically include a fluid delivery system for delivering and injecting selected fluids into an array cartridge which includes a hybridization chamber having a polymer array incorporated therein. They further include several systems such as a fluid mixing system for mixing fluids within the hybridization chamber, a temperature control system for monitoring and controlling the temperature of the fluids within the hybridization chamber, and a process control system for monitoring and selectively controlling the previously mentioned systems. The fluidics station is operated to deliver reagents and samples (e.g. analytes) to the hybridization chamber to perform the hybridization reactions. Following the hybridization, the fluidics station typically delivers a wash solution, an/or buffer to the hybridization chamber, to rinse substantially all of the sample containing solution from the chamber. Wash steps will generally be repeated to sufficiently reduce or eliminate any remaining, unhybridized target, typically two to ten times.

This invention relates to wash stations that are configured to reduce operating cycle times when processing large numbers of array cartridges. In this way, one or more washing steps may be performed in a rapid and efficient manner in order to increase the quantity of array cartridges to be processed according to a given procedure.

SUMMARY OF THE INVENTION

According to the invention, array cartridges may be washed in a simplified washing station. Conveniently, the wash steps may be performed independently of a fluidics station where hybridization reactions occur. In this way, a fluidics station may be used to carry out reactions while a separate washing station is used for the washing steps, thereby increasing the throughput of processed cartridges.

In one embodiment, a washing system comprises a support for holding at least one cartridge having a chamber with an inlet and an outlet, and at least one wash block movably coupled to the support. The wash block has an inlet needle and an outlet needle. These needles are configured such that the inlet needle penetrates the inlet of the chamber and the outlet needle penetrates the outlet of the chamber when the cartridge is held by the support and the wash block is moved towards the support.

In another embodiment, a method is provided for circulating a liquid through at least one cartridge that includes a chamber having an inlet and an outlet. According to the method, the cartridge is coupled to a support, and a wash block having an inlet needle and an outlet needle is moved towards the support until the inlet needle penetrates the inlet of the chamber and the outlet needle penetrates the outlet of the chamber. A liquid is supplied to the chamber via the inlet needle and the liquid is removed from the chamber via the outlet needle.

Washing systems and methods according to the invention allow the array cartridges to be washed independently of a fluidics station. Hence, a fluidics station may be used to perform hybridization reactions on new array cartridges while the subsequent wash steps of previously hybridized array cartridges are performed in parallel using the washing system. Thus, the invention results, advantageously, in significant time saving in the process. Further, the washing systems and methods according to the invention do not require the use of a computer workstation for operation.

One will understand that the washing systems and methods of the invention may be used for washing not only array cartridges having a hybridization chamber, but also various types of cartridges having at least one chamber with an inlet and an outlet. Further, although the washing systems and methods according to the invention may be used independently, they may also be incorporated or implemented in fluidics stations or in apparatuses performing other functions. Further, the methods of the invention may be used with liquids other than a wash solution.

BRIEF DESCRIPTION OF THE DRAWINGS

FIGS. 1a to 1d show respectively a front view, a side view, an end view and a rear view of an array cartridge having a chamber that may be used with a washing system according to the invention.

DESCRIPTION OF THE SPECIFIC EMBODIMENTS

Figure 2:
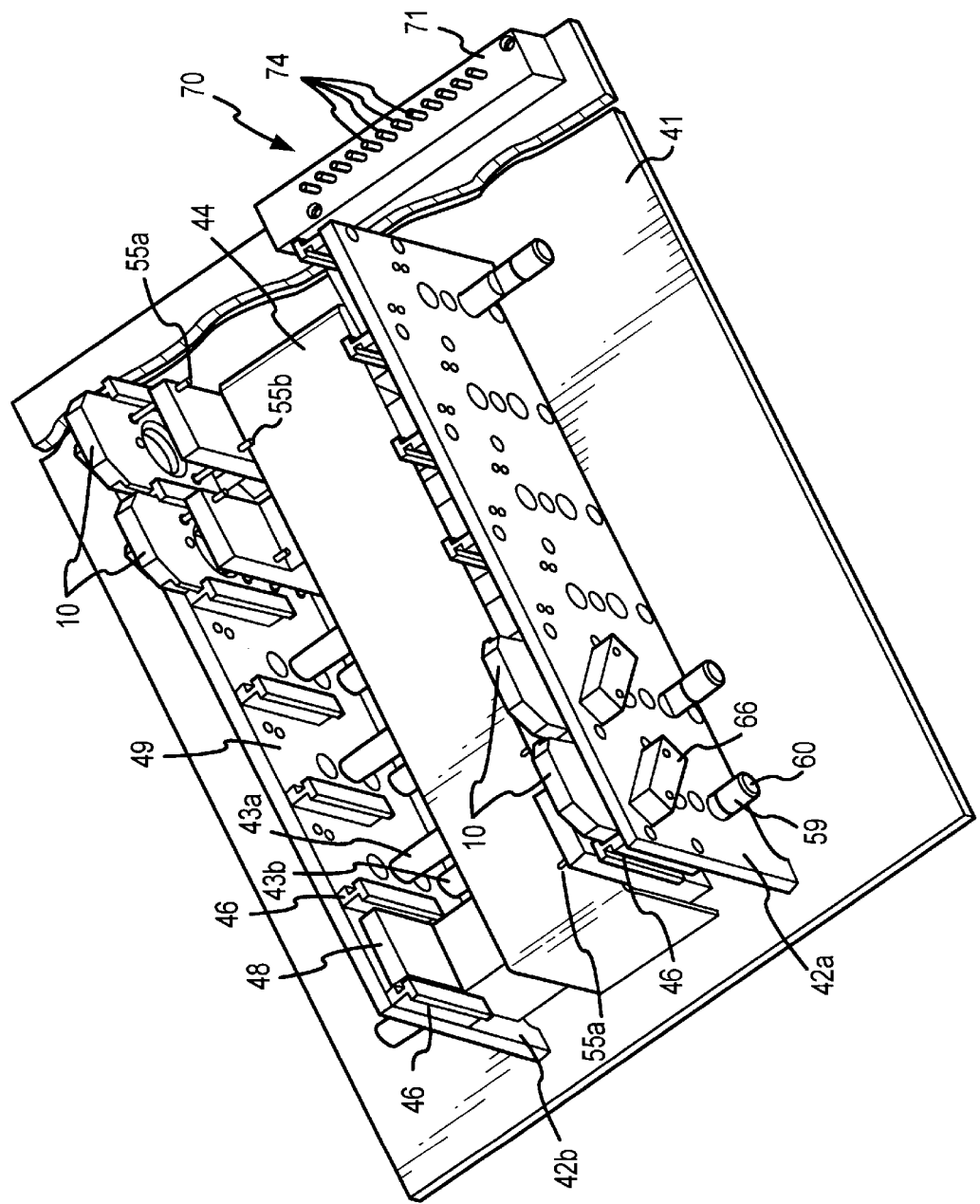
FIG. 2 shows a perspective view of a washing system according to a preferred embodiment of the invention which is adapted for washing cartridges of FIGS. 1a–1d.

The invention provides systems and methods for washing the chambers of a plurality of cartridges. The systems and methods may be used to simultaneously wash the chambers of essentially any type of cartridge having an inlet port and an outlet port that provide access to a chamber. Exemplary types of cartridges that may be used with the invention include, but are not limited to, those described in U.S. Pat. No. 5,945,334 and in co-pending U.S. application Ser. Nos. 08/624,312 and 08/528,173 and PCT Application No. WO95/33846, the disclosures of which are herein incorporated by reference. Such cartridges may include a pair of closed spaced apart planar walls that define a chamber. For example, when used as a hybridization chamber, the walls may be separated by a distance in the range from about 0.5 mm to about 2.0 mm. The systems of the invention may be used to wash about 2 to about 12 of such cartridges simultaneously. Advantageously, such systems may be operated without the need for an expensive controller.

FIGS. 1a–1d show a polymer array cartridge 10 of the type that may be used with the previously-mentioned fluidics stations and with a washing system according to the invention as described hereinafter. Cartridge 10 includes a front 14, a rear 16, and a cavity 12 which is defined in part by a generally planar face 18. Positioned across cavity 12 is an array chip (not shown). When the array chip is positioned over cavity 12, a hybridization chamber is formed. The hybridization chamber is generally rectangular or square in geometry and has a narrow width as defined by the distance between planar face 18 and the array chip. Extending between face 18 and the array chip are sides that intersect with each other to form corners and which further define the chamber. The distance between face 18 and the array chip may be e.g. in the range from about 0.5 mm to about 2.0 mm. Further, face 18 may have a length of about 5 mm to about 15 mm and a width of about 5 mm to about 15 mm. An inlet port 20 and an outlet port 22 are included in rear 16 to allow various fluids to be introduced into and removed from the hybridization chamber. For circulating liquid through the hybridization chamber, inlet port 20 and outlet port 22 are designed receive injection needles, i.e. hollow needles. For this purpose, each port 20, 22 may include a septum for sealing the port when an injection needle is inserted therein. A collar may optionally be fit around the injection needle, with the collar being slightly compressed by the cartridge surface around port 20 or 22 when the needle is inserted in the port. This collar provides an additional seal when the injection needle is inserted in a port of the cartridge.

Rear 16 further includes a cavity 24, located adjacent the array, which is adapted for receiving a temperature monitoring and/or controlling device employed in other applications. Cartridge 10 includes a pair of sides 26 and 28, a top 30 and a bottom 32. Extending from side 28 is an edge 34 that permits insertion of cartridge 10 in a carrier in only one orientation.

Figure 3:
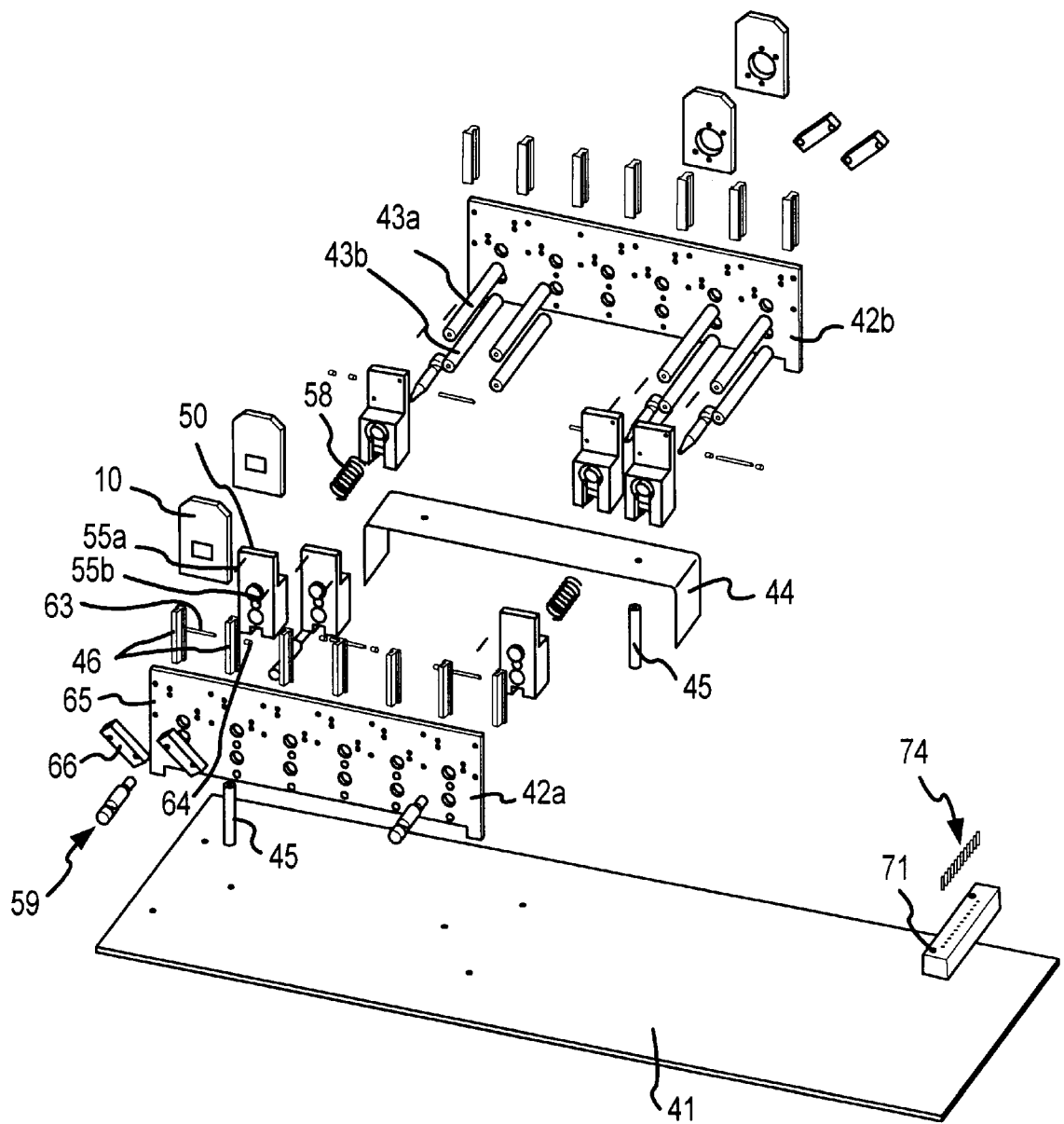
FIG. 3 shows an exploded view of the washing system of FIG. 2.

Referring now to FIGS. 2 and 3, a washing system according an embodiment of the invention will be described. The washing system is particularly designed for circulating a liquid, e.g. a wash solution, through the hybridization chamber of one or more cartridges 10 of FIGS. 1a–1d. The washing system comprises a horizontal base plate 41. Two vertical support plates 42a and 42b are fixed rigidly on base plate 41 by one or more securing mechanisms, e.g., screws. Support plates 42a and 42b are arranged parallel to each other and define a longitudinal direction. Each support plate 42a, 42b has a plurality of locations for each receiving a cartridge 10, with the locations being adjacent to one another along the support plate. In the depicted embodiment, each support plate 42a, 42b may receive up to six cartridges 10; for sake of clarity, only two cartridges 10 are shown for each support plate 42a, 42b on FIGS. 2 and 3. Each of the locations define a corresponding washing station for one cartridge 10. All of the washing stations may be identically designed. Further, support plate 42b with its washing stations is identical to support plate 42a with its washing stations, except that support plate 42b with its washing stations is rotated by 180° with respect of a vertical axis so that washing stations of support plate 42b face the washing stations of support plate 42a. Thus, for convenience of discussion, only one washing station of the washing system will be described.

Figure 4:
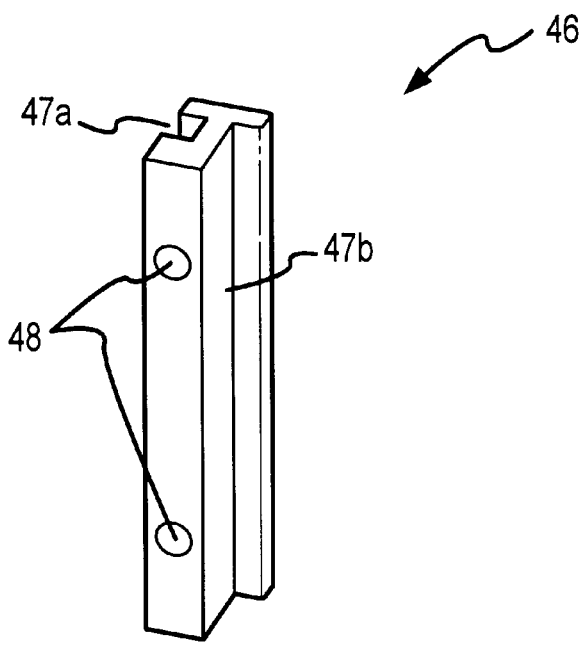
FIG. 4 shows a perspective view of a profiled rail used in the washing system of FIG. 2.

The leftmost washing station of support plate 42a will first be described. In so doing, reference numerals are only indicated for the leftmost washing station of support plate 42a, except if specified differently. The washing station comprises two profiled rails 46 arranged on support plate 42a on the face towards support plate 42b. Profiled rails 46 extend parallel to each other and are preferably vertically arranged. On FIG. 2, only the leftmost profiled rail 46 of support plate 42a is visible; for purpose of illustration, profiled rails 46 of the leftmost washing station of support plate 42b have also been referenced. As can be seen on FIG. 4, each profiled rail 46 defines two grooves 47a and 47b along the rail that preferably extend parallel to each other. Two walls of groove 47b are defined by profiled rail 46, and the third is advantageously defined by the surface of support plate 42a on which it is mounted. Profiled rails 46 are mounted on support plate 42a with the help of, e.g. two screws arranged through two through holes 48 of profiled rail 46.

Groove 47a is shaped correspondingly to side 28, more particularly to edge 34, of cartridge 10, and groove 47b is shaped correspondingly to side 26 of cartridge 10. The distance between profiled rails 46 when mounted on support plate 42a is configured to permit a cartridge 10 to be slidably inserted between groove 47b of the rail 46 located on the left and groove 47a of the rail 46 located at the right. When inserted, edge 34 of cartridge 10 engages groove 47a and side 26 of cartridge 10 engages groove 47b. Thus, profiled rails 46 with support plate 42a define a slot 49 for receiving a cartridge 10. For sake of clarity, reference numeral 49 on FIG. 2 is only indicated for the third slot (from the left side on) of support plate 42b instead of the leftmost slot of support plate 42a. Due to the correspondence between groove 47a and edge 34 of cartridge 10, cartridge 10 can be inserted in only one specific orientation in slot 49, i.e. with front face 14 facing support plate 42a and with edge 34 on the side of groove 47a. Thus, an improper orientation of cartridge 10 in slot 49 which may damage cartridge 10 or the needles of the washing station is avoided. One will understand that each profiled rail 46, except for the one at each end of support plates 42a and 42b, is used in two successive washing stations since its groove 47a is used for a given washing station and its groove 47b is used for the following washing station.

The washing station comprises a wash block 50 movably coupled, preferably in slidable manner, to support plate 42a. Wash block 50 has an inlet needle 55a and an outlet needle 55b for being coupled, respectively, to inlet port 20 and outlet port 22 of a cartridge 10 inserted in slot 49 when wash block 50 is moved towards cartridge 10. For sake of clarity, wash blocks are only drawn for the two leftmost washing stations of support plate 42a and the leftmost and the two rightmost washing stations of support plate 42b. Only needle 55a is visible for the leftmost washing station of support plate 42a on FIG. 2. For convenience of illustration, needles of the rightmost washing station of support plate 42b have also been referenced 55a, 55b on FIG. 2. The washing station may comprise two cylindrical guiding rods 43a and 43b extending parallel to each other from support plate 42a to support plate 42b. Guiding rods 43a and 43b of the leftmost washing station of support plate 42a are not visible on FIG. 2. However, the guiding rods of the second to fourth washing stations (from the left side on) of support plate 42b are visible partly. For purpose of illustration, those of the second washing station have been referenced 43a and 43b on FIG. 2. Guiding rods 43a and 43b are mounted on support plate 42a between the two rails 46 and extend perpendicular to support plates 42a and 42b. Guiding rods 43a and 43b are preferably located in a vertical plane in order to save space in the longitudinal direction. Guiding rods 43a and 43b allow, among other reasons, support plates 42a and 42b to be rigidly fixed to each other.

Wash block 50 is slidably mounted on guiding rods 43a and 43b. As such, a lower part 53b of wash block 50 has a through hole 51 and a through groove 52 arranged in the bottom face of wash block 50. Conveniently, groove 52 extends parallel to hole 51 (see FIGS. 5a–5b). Upper guiding rod 43a extends through hole 51, the diameter of which is adjusted for slidably receiving guiding rod 43a. Lower guiding rod 43b goes through groove 52, the width of which is adjusted for slidably receiving guiding rod 43b. The two opposite faces of groove 52 avoid rotation of wash block 50 around upper guiding rod 43a by abutting lower guiding rod 43b.

Conveniently, a pair of guiding rods 43a and 43b may be advantageously common to two washing stations, one station being part of support plate 42a and the other being part of support plate 42b and facing the first one. In other words, the wash blocks 50 of two facing washing stations are mounted on the same pair of guiding rods 43a and 43b.

A horizontal cover plate 44 may be arranged between support plates 42a and 42b such that cover plate 44 extends above guiding rods 43a and 43b of all the washing stations. The left and right edges of cover plate 44 preferably each terminate in a vertical wing oriented towards base plate 41. Cover plate 44 is fixed on base plate 41 via two longitudinally spaced apart vertical spacers 45 with help of, e.g. screws. (Spacers 45 are not visible on FIG. 2). The longitudinal edge of cover plate 44 defines an abutment for wash block 50. Thus, wash block 50 may slide between support plate 42a and cover plate 44.

The side of wash block 50 which faces support plate 42a is referred to as side 56a, while the opposite side is referred to as side 56b. Two through holes 54a and 54b are arranged in an upper portion 53a of wash block 50. Holes 54a and 54b extend parallel to hole 51. Inlet needle 55a and outlet needle 55b are mounted respectively, e.g. in press fit manner, in hole 54a and hole 54b. Needles 55a, 55b project from each side 56a, 56b of upper portion 53. Needles 55a, 55b are hollow in order to define a channel for flowing a liquid. Needles 55a, 55b are preferably straight.

In operation, the end of inlet needle 55a and outlet needle 55b sealing engage inlet port 20 and outlet port 22, respectively, of cartridge 10 when inserted in slot 49. A collar may optionally be fit around needles 55a, 55b to provide an additional seal, as previously described in relation with FIGS. 1a–1d. A tube (not shown) is sealingly fitted on the other end of each needle 55a, 55b, i.e. the ends on side 56b. Upper portion 53a may advantageously be thinner than lower part 53b to reduce the length of needles 55a, 55b and to facilitate their connection to tubing. The tube fitted on needle 55b goes, e.g. to a waste container, which may be placed adjacent to the right side of support plates 42a, 42b. The tube fitted on needle 55a is connected to an outlet port of a pump (not shown). The pump may conveniently be placed or fixed on base plate 41, preferably on a mid region between the waste container and the right edge of base plate 41. An inlet port of the pump is connected to an outlet port of a manifold 70 which in turn is connected to a bottle containing a wash and/or buffer solution (not shown). Alternatively, the inlet port of the pump may also be connected directly to such a bottle.

Figure 7:
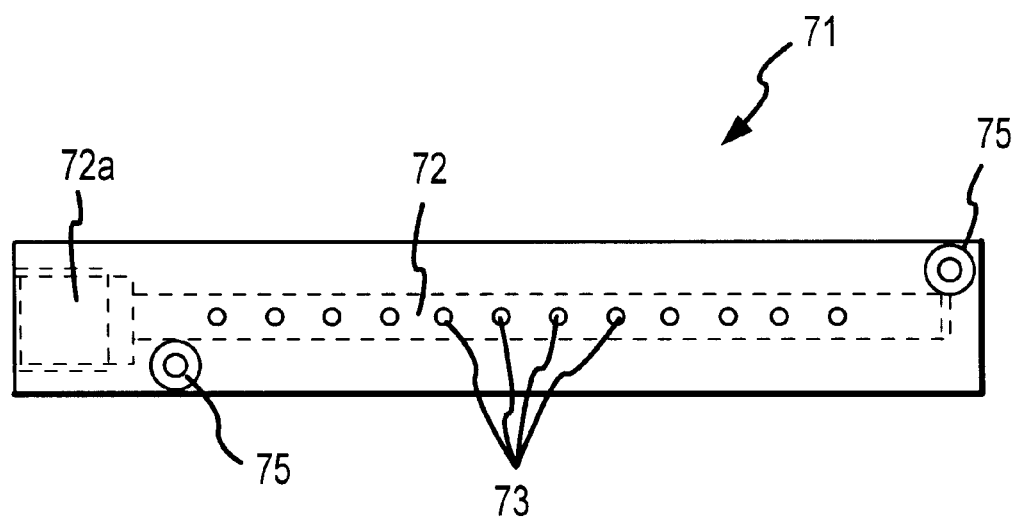
FIG. 7 is an end view of a manifold used in the washing system of FIG. 2.

Manifold 70 may be common to all washing stations of the washing system. Manifold 70 may be mounted on the right end region of base plate 41, aside of the pump. Manifold 70 comprises a base member 71 which is illustrated in FIG. 7. Base member 71 comprises a longitudinal non-through hole 72. The opening 72a of hole 72 defines an inlet port for manifold 70. An inlet tube (not shown) is coupled to opening 72a in a conventional manner, with the other end of the tube being connected to the previously-mentioned bottle. A plurality of holes 73 are arranged on a face of base member 71 in spaced relationship with each other. The number of holes 73 preferably corresponds to the number of washing stations of the washing system, with each hole 73 meeting hole 72. A hollow pin 74 is sealingly mounted in each hole 73. The end of each pin 74 projecting out of base member 71 defines an outlet port of manifold 70 on which is mounted a tube, the other end of which is connected to the inlet port of the pump. Hence, a sole bottle may be used to feed the several inlet ports of the pump with liquid. In turn, the pump feeds each needle 55a of the washing stations. Manifold 70 may be mounted on base plate 41 by screws (not shown) through two further holes 75 arranged in base member 71. Of course, holes 75 do not meet holes 71 and 72 to avoid leakage.

Alternatively, a pump may be used with one sole inlet port and a corresponding outlet port. In this case, the tube fitted on each needle 55a is connected via a tube directly to a respective outlet port of manifold 70, while inlet port 72a is connected to the outlet port of the pump and the inlet port of the pump is connected to the bottle.

Wash block 50 may further include a protuberance 76 on side 56a which corresponds to the shape of cavity 24 of cartridge 10. When moving wash block 50 towards cartridge 10 inserted in slot 49, the operator places cartridge 10 at a vertical position in slot 49 so that protuberance 76 engages cavity 24. In this way, cartridge 10 is correctly positioned in the vertical direction with respect to wash block 50. More particularly, inlet and outlet ports 20, 22 are correctly positioned with respect to needles 55a, 55b. Further, protuberance 76 advantageously bears the weight of cartridge 10 instead of needles 55a, 55b. The length of needles 55a, 55b is preferably determined so that needles 55a, 55b engage inlet and outlet ports 20, 22 only after protuberance 76 has engaged cavity 24. Alternatively, protuberance 76 may be omitted in which case the operator places cartridge 10 vertically with respect to wash block 50. In such a case, needles 55a, 55b may be designed for bearing the weight of cartridges 10 when filled with solution. Protuberance 76 may also be replaced by an abutment arranged either on support plate 42a or on wash block 50. In this case, bottom 32 of cartridge 10, when inserted in slot 49, rests on the abutment, thereby vertically positioning cartridge 10 with respect to wash block 50.

When arranged on support plate 42a, the abutment may be located between profiled rails 46 or in one or both of grooves 47, 47b. When arranged on wash block 50, the abutment may project from side 56a of wash block 50. In this case, the abutment projects from side 56a to a greater extent than needles 55a, 55b so that when moving wash block 50 towards cartridge 10, the operator may release cartridge 10 once this abutment comes under bottom 32 while needles 55a, 55b have not yet engaged ports 20, 22. In this way, the cartridge 10 is positioned on the abutment before needles 55a, 55b engage ports 20, 22.

Wash block 50 is sufficiently movable away from support plate 42a so that needles 55a, 55b (and protuberance 76 if relevant) are out of slot 49. Such movement allows for the insertion and removal of cartridge 10.

Figure 6:
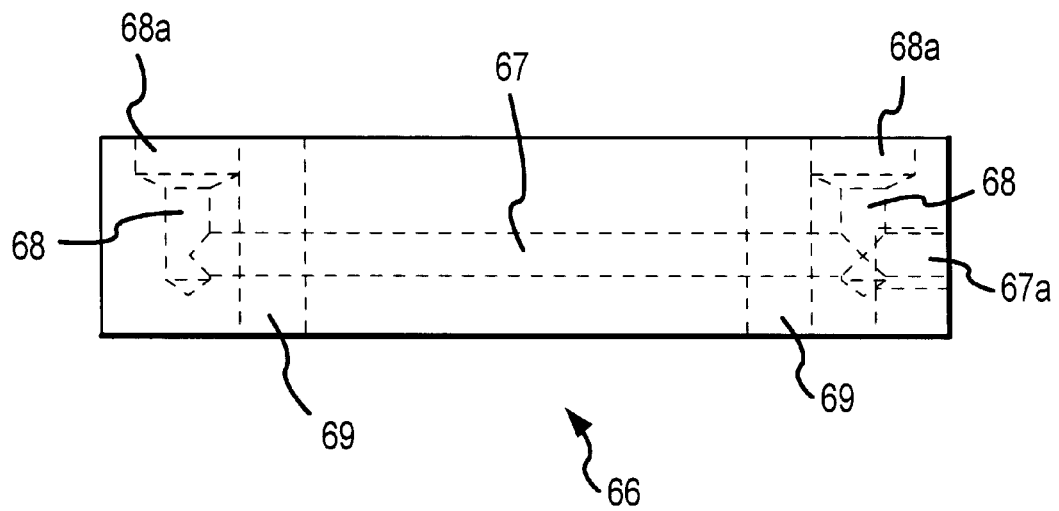
FIG. 6 is a front view of a bypass member used in the washing system of FIG. 2.

In the absence of cartridge 10 in slot 49 of a washing station, the washing station may include a bypass circuit to connect inlet needle 55a to outlet needle 55b. In this way, liquid circulated by the pump will not spill onto the washing system when cartridges 10 are inserted in only some of the washing stations. To access the bypass circuit, wash block 50 may be pressed against support plate 42a until each needle 55a, 55b enters a respective through hole 65 arranged on support plate 42a. A bypass member 66 is mounted on the side of support plate 42a opposite to wash block 50 and covers holes 65. Bypass members 66 are represented only for the two leftmost washing stations of support plate 42a in FIG. 2. As shown in FIG. 6, bypass member 66 may comprise a longitudinal non-through hole 67, an opening 67a of which is sealingly closed by use of, e.g. of a cap (not shown) that is screwed or glued into opening 67a. Two parallel non-through holes 68 intersect with hole 67. In this way, holes 67 and 68 define a channel for circulating liquid. Holes 68 are spaced apart from each other so as to correspond with holes 65 of support plate 42a. Bypass member 66 is mounted on support plate 42a by securing mechanism, such as screws, passing through two further holes 69 of bypass member 66. Of course, holes 69 do not meet holes 67 and 68 to avoid liquid leakage. An opening 68a of each hole 68 is adapted to receive an O-ring which is further maintained by the surface of support plate 42a around the corresponding hole 65. When moved towards support plate 42a, needles 55a, 55b penetrate hole 65 and then hole 68 through the corresponding O-ring which provides a seal between bypass member 66 and needle 55a and 55b. Alternately, the bypass circuit may be constructed of a flexible tube mounted by the operator on needles 55a, 55b in order to link them when no cartridge 10 is processed by the corresponding washing station.

Figure 5A:
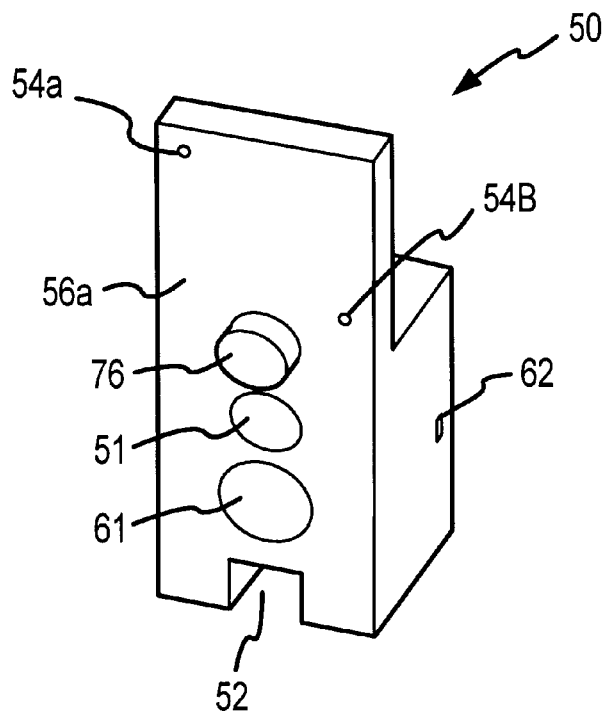
FIGS. 5a and 5b show respectively a perspective view seen from the front and from the rear of a wash block used in the washing system of FIG. 2.
Figure 5B:
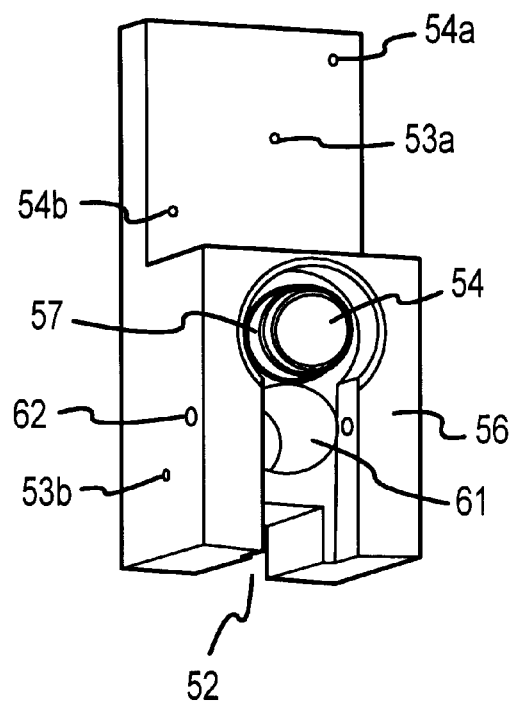

Wash block 50 may be resiliently pushed or pulled toward or away from support plate 42a. This may be accomplished as follows. As shown in FIGS. 5a and 5b, wash block 50 comprises a collar 57 arranged around hole 51 on side 56b of wash block 50. The external circumference of collar 57 defines a seat for a helical spring 58. Spring 58 is visible in FIG. 3. Upper guiding rod 43a passes axially through spring 58. Further, spring 58 preferably extends from the collar 57 of one of wash blocks 50 of a washing station of support plate 42a to a corresponding collar 57 of the wash block 50 of the washing station of support plate 42b. Thus, spring 58 resiliently pushes each of wash blocks 50 towards its corresponding support plate 42a or 42b.

Alternatively, this resilient press feature of wash block 50 may be accomplished by use of a mechanical lock to selectively lock wash block 50 either in the position with its needles 55a, 55b coupled to ports 20, 22 of cartridge 10 in slot 49, or in the position with its needles 55a, 55b coupled to bypass member 66 when no cartridge 10 is inserted in slot 49. In this way, wash block 50 cannot slide on guiding rods 43a, 43b during operation to avoid spillage of liquid by disengagement of needles 55a, 55b.

The washing station may further comprise a handling rod 59. Handling rod 59 has a generally cylindrical shape. For convenience of illustration, handling rods have been drawn for only some washing stations in FIGS. 2 and 3. Handling rod 59 extends slidably through a corresponding hole arranged in support plate 42a. Handling rod 59 projects out of support plate 42a on the side opposite to wash block 50 where it terminates in a knob 60 adapted for manipulation by an operator. On the other side of support plate 42a, handling rod 59 extends into a through hole 61 arranged in lower part 53b of wash block 50. Hole 61 is parallel to hole 51 and is arranged between hole 51 and groove 52. Handling rod 59 is linked to wash block 50 by a pin 63 traversing a through hole 62 of the wash block 50 perpendicularly to the axis of hole 61. Pin 63 further traverses a through hole in the end region of handling rod 59. Pin 63 is preferably mounted in press-fit manner in hole 62. As the diameter of hole 61 may be larger than the diameter of the end of handling rod 59, two hollow spacers 64 traversed by pin 63 may be interposed between each side of handling rod 59 and the corresponding surface of wash block 50 surrounding hole 62 on each side of hole 61. Only one spacer 64 is indicated on FIG. 3. In this way, handling rod 59 allows the operator to push wash block 50 away from support plate 42a against spring 58.

The different parts of the washing stations may be constructed of conventional materials. For example, plates 41, 42a, 42b and 44 may be made of aluminum. Bypass members 66 and base member 71 may be made of a plastic material, preferably of a transparent type, e.g. PMMA. In this way, it is possible to see if liquid is circulating through them. Needles 55 and pins 74 may also be made of a plastic material. The various tubing is preferably of a flexible type and may be transparent.

A method for washing one or more cartridges 10 with the washing station of FIG. 2 will next be described. First, it may be convenient to rinse the liquid circuits of the washing system. For this purpose, all slots 49 are free, i.e. without cartridges 10 in them, and wash blocks 50 have their inlet needle 55a and outlet needle 55b in bypass communication. In other words, wash blocks 50 are against their respective support plates 42a or 42b with their needles 55a, 55b inserted in holes 68 of bypass member 66 in order to be in communication. The operator connects the inlet tube of manifold 70 into a bottle with double distilled water or a similar liquid. The pump is turned on to fill the lines of the washing system with water. Afterwards, the operator preferably reverses the flow of the pump to empty the different lines. The tubes connected to needles 55b which go to the waste container are preferably not immersed in the liquid present in the waste container in order to avoid drawing this liquid back into the lines of the washing system. Because the tubes are transparent, the operator may easily check if bypass members 66 are empty. This avoids spilling of water on the washing system or on cartridges 10 when inserted in slots 49.

After this optional step of rinsing, the operator may simultaneously carry out a washing step on one or more cartridges 10 in the following way. First, the operator inserts each cartridge 10 to be washed in any one of the washing stations of the washing system. Therefore, for each cartridge 10, a slot 49 of a washing station is freed from wash block 50. This may be accomplished by pressing on knob 60 of handling rod 59 to separate wash block 50 from its support plate 42a or 42b. Then, the operator inserts a cartridge 10 in slot 49 and moves the corresponding wash block 50 towards its support plate by releasing handling rod 59. This causes protuberance 76 to engage cavity 24 of cartridge 10 and causes needles 55a, 55b to engage inlet and outlet ports 20, 22. Wash blocks 50 of the washing stations without cartridges 10 remain in bypass communication.

The operator connects the inlet tube of manifold 70 into a bottle containing a wash solution and turns on the pump to flow the wash solution through the cartridges 10 and evacuate the liquid to the waste container. The bottle of wash solution is preferably placed on an elevated stage with respect to the pump for generating a low hydrostatic pressure. After the wash solution has been circulated for a desired time, the pump is stopped, either automatically or by the operator. The flow of the pump may also be reversed for a time to remove the wash solution from the lines of the washing system.

The cartridges 10 are then removed from slots 49. This may be accomplished by pressing the corresponding handling rod 59 to disengage wash block 50 from a given cartridge 10. Cartridge 10 is then lifted out of slot 49. Once cartridge 10 is removed, the operator may release handling rod 59 to permit wash block 50 to move back towards its support plate 42a or 42b. In this way, needles 55a, 55b penetrate holes 68 of bypass member 66 under the action of spring 58. When all cartridges 10 are removed, it may be convenient to again perform a rinsing step in the same way as already described.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A washing system comprising:
   a support for holding at least one cartridge including a chamber having an inlet and an outlet; and
   at least one wash block movably coupled to the support and having an inlet needle and an outlet needle;
   wherein the inlet needle penetrates the inlet of the chamber and the outlet needle penetrates the outlet of the chamber when the cartridge is held by the support and the wash block is moved towards the support.

2. A system as in claim 1, further comprising tubing coupled to the inlet needle.

3. A system as in claim 2, further comprising a supply of liquid supplying the tubing coupled to the inlet needle.

4. A system as in claim 3, further comprising a manifold disposed between the supply of liquid and the tubing coupled to the inlet needle.

5. A system as in claim 3, further comprising a pump circulating liquid from the supply of liquid to the inlet needle.

6. A system as in claim 1, further comprising tubing coupled to the outlet needle.

7. A system as in claim 1, wherein the wash block is resiliently urged against the support with a spring.

8. A system as in claim 1, further comprising a handling rod connected to the wash block.

9. A system as in claim 8, wherein the handling rod passes through the support.

10. A system as in claim 1, wherein the wash block has a protuberance for positioning the cartridge held by the support when the wash block is moved towards the support.

11. A system as in claim 1, wherein the support comprises a wall having a slot for receiving the cartridge.

12. A system as in claim 1, further comprising a member coupled to the support and having a channel, the inlet needle and the outlet needle penetrating in said channel when the wash block is moved towards the support free of a cartridge.

13. A system as in claim 1, wherein the support is asymmetrical to hold the cartridge in only one orientation.

14. A system as in claim 1, wherein the wash block is slidably coupled to the support.

15. A system as in claim 1, wherein the wash block is slidably mounted on at least one guiding rod of the support.

16. A system as in claim 15, further comprising at least a second wash block slidably mounted on the guiding rod, wherein the support is adapted to hold at least a second cartridge, the needles of the second wash block penetrating the inlet and the outlet of the second cartridge when the second cartridge is held by the support and the second wash block is moved towards the support.

17. A system as in claim 16, further comprising a spring arranged around the guiding rod between the first wash block and the second wash block, wherein the spring urges the first wash block and the second wash block towards the support.

* * * * *